United States Patent [19]

Borrett

[11] Patent Number: 4,861,893

[45] Date of Patent: Aug. 29, 1989

[54] CHEMICAL PROCESS

[75] Inventor: Gary T. Borrett, Harlow, England

[73] Assignee: Beecham Group PLC., Brentford, United Kingdom

[21] Appl. No.: 894,765

[22] Filed: Aug. 8, 1986

[30] Foreign Application Priority Data

Aug. 10, 1985 [GB] United Kingdom ................ 8520154

[51] Int. Cl.$^4$ .................. C07D 211/02; C07D 211/82; C07D 213/133; C07D 213/55
[52] U.S. Cl. .................................... 546/185; 546/321; 546/322
[58] Field of Search ............... 546/185, 322, 321, 228, 546/251, 322

[56] References Cited

U.S. PATENT DOCUMENTS 4,007,196  2/1977  Christensen et al. .......... 260/293.58

FOREIGN PATENT DOCUMENTS 336414   5/1921  Fed. Rep. of Germany .
574137   3/1933  Fed. Rep. of Germany .
2658804  7/1978  Fed. Rep. of Germany .
369132   6/1963  Switzerland .
1396681  6/1975  United Kingdom .

OTHER PUBLICATIONS

Noller, "Chemistry of Organic Compounds", 3rd ed., (1965), p. 668.
Fieser et al., "Reagents for Organic Synthesis", (1975–vol. 5), p. 687.
Katritzky et al., "Comprehensive Heterocyclic Chemistry", (vol. 2–1984), p. 55.
C.A. 100: 34731n, Rosenberg et al., (1984).
C.A. vol. 100 (1984), Formula Index, p. 2422 F.
Barton, D. et al., Comprehensive Organic Chemistry, vol. 4, pp. 44, 50 (1979).
Ferles, M. et al., Advances in Heterocyclic Chemistry, vol. 12, p. 59 (1970).
Rylander, P., Hydrogenation Methods, pp. 148–149 (1985).
Rylander, P., Catalytic Hydrogenation in Organic Synthesis, p. 175 (1970).
House, H., Modern Synthetic Methods, pp. 216–218, (1972).
March, J., Advanced Organic Chemistry, p. 1101 (3d Ed. 1985).
Ederfield, R., Heterocyclic Compounds, V.I., pp. 635–637, (1950).
Rylander, P., Catalytic Hydrogenation over Platinum Metal, (1967); pp. 320–322.
Kaiser et al., J. Org. Chem., 49, pp. 4203–4209 (1984).
Wenkert, E. et al., "Tetrahydropyridines", J. Org. Chem., 33, (1968); pp. 747–753.

Primary Examiner—Joseph Paul Brust
Attorney, Agent, or Firm—James F. Haley, Jr.; Eric R. Hubbard

[57] ABSTRACT

A process is disclosed for the preparation of a compound of formula (I):

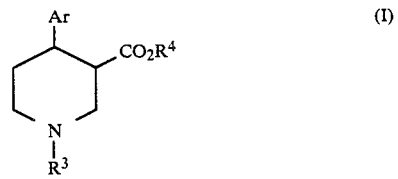

where Ar is aryl or substituted aryl and $R^3$ and $R^4$ are the same or different and each is alkyl, which process comprises hydrognating a compound of formula (II):

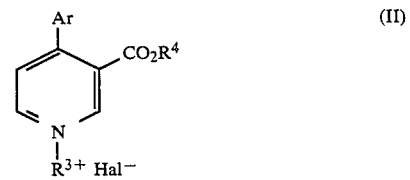

wherein Ar, $R^3$ and $R^4$ are as defined with respect to formula (I) and Hal is a halogen atom.

Compounds of formula (I) are useful as chemical intermediates.

8 Claims, No Drawings

CHEMICAL PROCESS

This invention relates to a novel chemical process for preparing aryl-piperidine esters and to novel intermediates used in that process.

British patent No. 1422263 and U.S. Pat. No. 4007196 disclose compounds of formula A

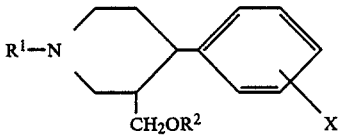

in which $R^1$ represents hydrogen, trifluoro ($C_{1-4}$) alkyl, alkyl or alkynyl, $R^2$ represents an alkyl or alkynyl group having 1–4 carbon atoms, or a phenyl group optionally substituted by $C_{1-4}$ alkyl, alkylthio, alkoxy, halogen, nitro, acylamino, methylsulfonyl or methylenedioxy, or represents tetrahydronaphthyl, and X represents hydrogen, alkyl having 1–4 carbon atoms, alkoxy, trifluoroalkyl, hydroxy, halogen, methylthio, or aralkyloxy.

The compounds of formula A are disclosed as having pharmacological properties that make them useful as anti-depressants.

One compound that has proved especially valuable is paroxetine ($R^1$=H, $R^2$=5-(1,2-benzdioxylyl), X=4-F) which is in the (−)-trans configuration.

In the above-mentioned patents, the compounds of formula A are prepared using an intermediate of formula B

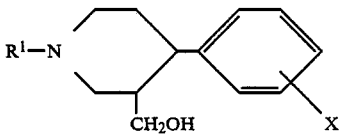

in which $R^1$ and X are as defined above.

The piperidine carbinols of formula B are prepared by reduction of an ester of formula C

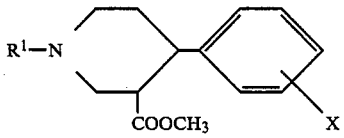

with a complex metal hydride reducing agent.

The compound of formula C is obtained by reacting arecoline (when $R^1$=methyl) or arecoline homologues with phenyl (or substituted phenyl) magnesium bromide. This procedure has the disadvantages that arecoline is a powerful irritant and that the ester of formula C is obtained as a mixture of cis and trans configuration compounds.

We have now discovered a new process for preparation of piperidine carbinol esters which advantageously avoids the use of arecoline and selectively produces the cis-isomer in a good overall yield.

Accordingly, the present invention provides a process for preparing a compound of formula I

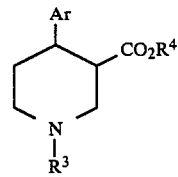

in which Ar represents an aryl or substituted aryl group and $R^3$ and $R^4$ each represents an alkyl group, by hydrogenation of a compound of formula II

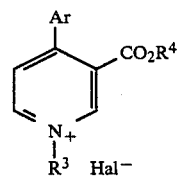

in which Ar, $R^3$ and $R^4$ are as defined for formula (I), and Hal represents a halogen atom.

In formulae I and II, Ar may be where X is as defined for formula A. Preferably X is fluorine or hydrogen and $R^3$ is methyl. The halogen Hal is preferably chloride or bromide.

The hydrogenation may be carried out conventionally as a catalytic hydrogenation, for example using a platinum oxide catalyst.

The compounds of formula I are obtained in the cis-configuration but as a mixture of enantiomers. The compounds may be resolved into their enantiomeric forms by conventional methods, such as by use of an optically active acid.

The compounds of formula I may optionally be converted to the trans-configuration by treatment with a base, for example sodium methoxide, in an inert solvent such as toluene.

The esters of formula I may be converted to the corresponding carbinols by conventional reduction, for example using a metal hydride such as lithium aluminium hydride. The cis-ester gives the cis-carbinol, and the trans-ester gives the trans-carbinol.

The carbinols obtained from the compounds of formula I may be used as intermediates in the preparation of compounds of formula A making use of the procedures set out in British Patent No. 1422263 or U.S. Pat. No. 4,007,196.

For example, to prepare paroxetine, the carbinol in which

Ar = (4-fluorophenyl)

and $R^3$=Me in the (+)-cis or (−)-trans configuration is reacted with thionyl chloride or benzenesulphonyl chloride and then with sodium 3,4-methylenedioxyphenoxide.

Subsequently the N-methyl group is replaced by reaction with phenyl chloroformate followed by de-acylation with KOH to obtain $R^3=H$.

The present invention also provides the intermediates of formula II as novel compounds. Preferred substituents are as exemplified for formula I.

The quaternary pyridines of formula II may be prepared from aryl-pyridines of formula III

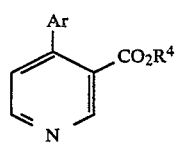

by quaternization under conventional conditions with an alkyl halide of formula $R^3$-Hal.

The aryl-pyridines of formula III may be prepared by reacting an alkyl, preferably methyl, nicotinate (formula IV) with a chloroformate ester, such as ethyl or phenyl chloroformate, and an aryl magnesium halide to give a dihydropyridine of formula V. The dihydropyridine (formula V) is then aromatized and the nitrogen atom de-protected in conventional manner, for example by heating with sulphur in decalin, to give the compounds of formula III. The procedure is illustrated in the following reaction scheme in which Ar, $R^4$ and Hal are as defined above and $R^5$ is an alkyl or aryl group.

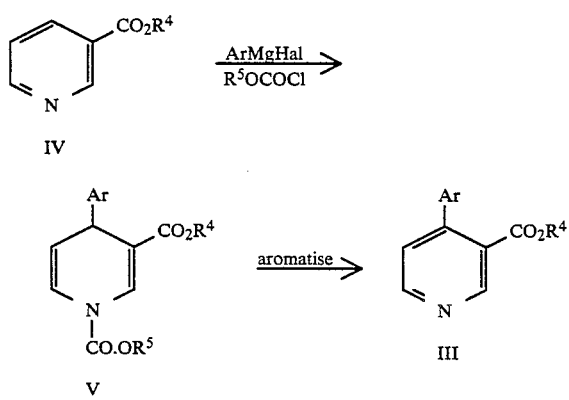

Certain of the intermediates described above are novel and, together with the above described processes for their preparation, they form part of the present invention.

In particular the present invention provides as novel compounds the compound of formula III in which Ar=4-fluoro-phenyl and $R^4$=methyl, and the compound of formula V in which Ar=4-fluoro-phenyl, $R^4$=methyl and $R^5$=ethyl.

As used herein, the terms alkyl, alkoxy, aralkyloxy and aryl include, but are not limited to, groups in which the alkyl moiety, when present, is a straight or branched alkyl group containing from 1 to 6 carbon atoms, more especially from 1 to 4 carbon atoms, and the aryl moiety when present, is phenyl.

The following Examples illustrate the preparation of novel intermediates of this invention (Example 1) and the novel process of this invention (Example 2a).

EXAMPLE 1

4-(4'-Fluorophenyl)-3-methoxycarbonyl-1-methyl-pyridinium bromide

Ethyl chloroformate (3.5 ml) was added to a stirred suspension of cuprous chloride (0.33 g) in dry tetrahydrofuran (100 ml) under nitrogen. After cooling to 0°, a solution of methyl nicotinate (5.0 g) in tetrahydrofuran (10 ml) was added slowly followed by the addition of 4-fluorophenyl magnesium bromide solution [from 4-bromo-fluorobenzene (4.4 ml) and magnesium (0.93 g) in tetrahydrofuran (25 ml)]. After stirring for 20 minutes, the mixture was diluted with ethyl acetate and decomposed by the addition of a saturated ammonium chloride/ammonia solution (1:1, 100 ml). The organic phase was washed with dilute acid and brine and dried over anhydrous sodium sulphate. Evaporation of the solvent gave 1,4-dihydro-1-ethoxycarbonyl-4-(4'-fluorophenyl)-3-methoxycarbonylpyridine as an off-white solid (10.37 g, 93%). A sample crystallised from ethyl acetate had m.p. 83-85°.

The crude dihydropyridine (10.37 g) was dissolved in warm decalin (25 ml) and sulphur (1.04 g) added. The mixture was refluxed under nitrogen for 16 hours, then cooled and diluted with ethyl acetate (100 ml) and extracted with dilute hydrochloric acid (4×25 ml, 2M). The aqueous acid extracts were washed with ethyl acetate (20 ml), basified with 20% sodium hydroxide solution and extracted with dichloromethane (50 ml and 3×25 ml). The organic solutions were dried (potassium carbonate) and evaporated to give 4-(4'-fluorophenyl)-3-methoxycarbonylpyridine as an oil which rapidly crystallized (5.98 g, 76%). A sample crystallized from ethyl acetate had m.p. 94°-95°.

The crude pyridine (5.95 g) was treated with methyl bromide (2.2 ml) in acetone (25 ml). After heating in a sealed vessel at 53° for 60 hours and cooling to 0°, the title pyridinium salt was collected by filtration, washed with acetone and dried (7.4 g, 88%), m.p. 165°-170° (decomp.).

| $^1$H-n.m.r. (CDCl$_3$) |
| --- |
| δ = 3.84 (s, 3H) |
| 4.86 (s, 3H) |
| 7.23 (m, 2H) |
| 7.44 (m, 2H) |
| 8.08 (d, J = 7 Hz, 1H) |
| 9.58 (s, 1H) |
| 9.88 (d, J = 7 Hz, 1H) |

EXAMPLE 2

(a)

(±)-cis-4-(4'-Fluorophenyl)-3-methoxycarbonyl-1-methyl-piperidine 4-(4'-Fluorophenyl)-3-methoxycarbonyl-1-methyl-pyridinium bromide (15.90 g), prepared as in Example 1, in ethanol (250 ml) was hydrogenated at atmospheric pressure and 45° for 24 hours, in the presence of platinum oxide (0.5 g). Evaporation of the filtrate after removing the catalyst gave a dark oil which was partitioned between 10% sodium carbonate solution (100 ml) and dichloromethane (30 ml). After separation, the aqueous phase was extracted with dichloromethane (3×20 ml) and the organic solutions dried (potassium carbonate) and evaporated to give an off-white solid (12.1 g). Crystallisation from ethyl acetate gave the title compound as white crystals (8.32 g, 72%), m.p. 88°–89°.

| $^1$H n.m.r. (CDCl$_3$) |
|---|
| δ = 1.75 − 3.30 (m, 8H) |
| 2.27 (s, 3H) |
| 3.50 (s, 3H) |
| 6.75 − 7.40 (m, 4H) |

(b) Isomerisation to (±)-trans-4-(4′-fluorophenyl)-3-methoxycarbonyl-1-methylpiperidine (±)-cis-4-(4′-Fluorophenyl)-3-methoxycarbonyl-1-methylpiperidine (2.0 g), prepared as in Example 2(a), in dry toluene was added to sodium methoxide in toluene and refluxed for 7 hours. After cooling to 0° and filtration, evaporation gave the title compound as an oil (1.97 g, 99%), purity 85–90%.

| $^1$H-n.m.r. (CDCl$_3$) |
|---|
| δ = 1.15 − 1.95 (m, 4H) |
| 2.30 (s, 3H) |
| 2.50 − 3.25 (m, 4H) |
| 3.40 (s, 3H) |
| 6.80 − 7.30 (m, 4H) |

I claim:

1. A process for the preparation of a compound of formula (I):

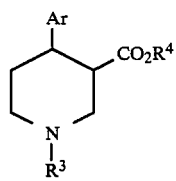

wherein Ar is a group:

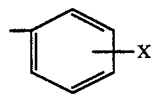

in which X is hydrogen, alkyl having 1–4 carbon atoms, alkoxy, trifluoroalkyl, hydroxy, halogen, methylthio, or aralkyloxy and R$^3$ and R$^4$ are the same or different and each is C$_{1-6}$ alkyl, which process comprises hydrogenating a compound of formula (II):

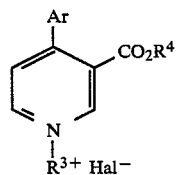

where Ar, R$^3$ and R$^4$ are as defined with respect to formula (I) and Hal is a halogen atom.

2. A process according to claim 1, further comprising the step of converting the compound of formula (I) from the cis- to the trans-configuration thereof.

3. A compound of formula (IIIa):

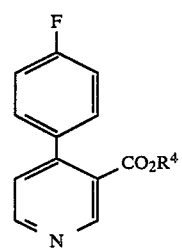

wherein R$^4$ is C$_{1-6}$ alkyl.

4. A process for the preparation of a compound of formula (IIIa):

(IIIa)

which process comprises aromatizing and deprotecting a compound of formula (Va):

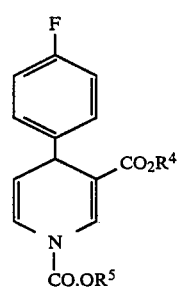

wherein R$^4$ is C$_{1-6}$ alkyl and R$^5$ is C$_{1-6}$ alkyl or phenyl.

5. A compound of formula (Va):

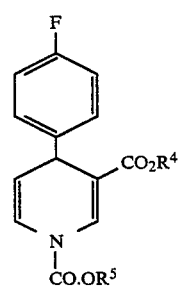

wherein R$^4$ is C$_{1-6}$ alkyl and R$^5$ is C$_{1-6}$ alkyl or phenyl.

6. A process for the preparation of a compound of formula (Va):

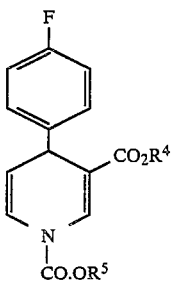
(Va)

which process comprises reacting a nicotinate ester of formula (IV):

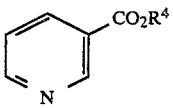
(IV)

wherein $R^4$ is $C_{1-6}$ alkyl with a chloroformate ester of formula $R^5OCOCl$, wherein $R^5$ is $C_{1-6}$ alkyl or phenyl, and a 4-fluorophenyl magnesium halide.

7. 4-(4′-fluorophenyl)-3-methoxycarbonyl-1-methylpyridinium bromide, 1,4-dihydro-1-ethoxycarbonyl-4-(4′-fluorophenyl)-3-methoxycarbonylpyridine, or 4(4′-fluorophenyl)-3-methoxycarbonylpyridine.

8. A compound of formula (II):

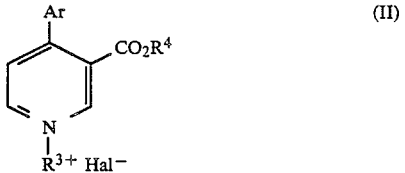
(II)

wherein Ar is a group:

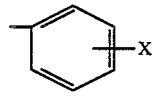

in which X is hydrogen, alkyl having 1–4 carbon atoms, alkoxy, trifluoroalkyl, hydroxy, halogen, methylthio, or aralkyloxy and $R^3$ and $R^4$ are the same or different and each is $C_{1-6}$ alkyl, and Hal is chlorine or bromine.

* * * * *

UNITED STATES PATENT AND TRADEMARK OFFICE
CERTIFICATE OF CORRECTION

PATENT NO. : 4,861,893

DATED : August 29, 1989

INVENTOR(S) : Gary T. Borrett

It is certified that error appears in the above-identified patent and that said Letters Patent is hereby corrected as shown below:

Title page, ABSTRACT, line 5, "hydrognating" should be
    -- hydrogenating --

Column 1, line 31, ")-)-trans" should be -- (-)-trans --

Column 2, line 65, ")-)-trans" should be -- (-)-trans --

Signed and Sealed this

Fifteenth Day of October, 1991

*Attest:*

HARRY F. MANBECK, JR.

*Attesting Officer*      *Commissioner of Patents and Trademarks*